(12) United States Patent
Tarassenko et al.

(10) Patent No.: US 9,874,472 B2
(45) Date of Patent: Jan. 23, 2018

(54) METHOD AND APPARATUS FOR MONITORING AND ANALYZING VIBRATIONS IN ROTARY MACHINES

(75) Inventors: Lionel Tarassenko, Oxford (GB); David A Clifton, Oxford (GB); Dennis King, Derby (GB); Steven P King, Swadlincote (GB); David J Ault, Castle Donington (GB)

(73) Assignee: ROLLS-ROYCE PLC, London (GB)

( * ) Notice: Subject to any disclaimer, the term of this patent is extended or adjusted under 35 U.S.C. 154(b) by 1002 days.

(21) Appl. No.: 13/201,082

(22) PCT Filed: Feb. 17, 2010

(86) PCT No.: PCT/GB2010/000281
§ 371 (c)(1),
(2), (4) Date: Sep. 27, 2011

(87) PCT Pub. No.: WO2010/094915
PCT Pub. Date: Aug. 26, 2010

(65) Prior Publication Data
US 2012/0035885 A1 Feb. 9, 2012

(30) Foreign Application Priority Data
Feb. 18, 2009 (GB) .................................. 0902730.1

(51) Int. Cl.
*G01H 1/00* (2006.01)
*G01H 3/08* (2006.01)
(Continued)

(52) U.S. Cl.
CPC .............. *G01H 1/006* (2013.01); *G01H 3/08* (2013.01); *G01M 13/028* (2013.01);
(Continued)

(58) Field of Classification Search
CPC ........ G01H 1/003; G01H 1/006; G01H 13/00; G01H 3/08; G01N 2291/2693;
(Continued)

(56) References Cited

U.S. PATENT DOCUMENTS 6,257,066 B1 7/2001 Chandler et al.
6,548,164 B1 4/2003 Bacon, Jr.
(Continued)

FOREIGN PATENT DOCUMENTS

EP 1 431 727 A2 6/2004

OTHER PUBLICATIONS

British Search Report issued in British Patent Application No. 0902730.1 dated Jun. 18, 2009.
International Search Report issued in International Patent Application No. PCT/GB2010/000281 dated May 26, 2010.
Written Opinion issued in International Patent Application No. PCT/GB2010/000281 dated May 26, 2010.

*Primary Examiner* — Gregory J Toatley
*Assistant Examiner* — Terence Stifter, Jr.
(74) *Attorney, Agent, or Firm* — Oliff PLC (57) ABSTRACT

Vibration amplitudes are recorded as a function of rotation speed and of frequency and the data is analyzed to estimate a noise floor amplitude threshold for each of a plurality of different speed and frequency sub-ranges. On the basis of training data known to be normal speed-frequency areas which contain significant spectral content in normal operation are deemed "known significant spectral content", so that during monitoring of new data points which correspond to significant vibration energy at speeds and frequencies different from the known significant spectral content can be deemed "novel significant spectral content" and form the basis for an alert. The estimation of the noise floor is based on a probabilistic analysis of the data in each speed-frequency area and from this analysis an extreme value distribution expressing the probability that any given sample is noise is obtained.

14 Claims, 11 Drawing Sheets

(51) Int. Cl.
    *G01N 29/46*     (2006.01)
    *G01M 13/02*     (2006.01)
    *G01M 13/04*     (2006.01)
    *G01M 15/12*     (2006.01)

(52) U.S. Cl.
    CPC .......... *G01M 13/045* (2013.01); *G01M 15/12* (2013.01); *G01N 29/46* (2013.01); *G01N 2291/2693* (2013.01)

(58) Field of Classification Search
    CPC .......... G01N 2291/2696; G01N 29/46; G01M 13/04; G01M 13/028; G01M 13/045; G01M 15/12
    USPC ......................................................... 702/183
    See application file for complete search history.

(56) References Cited

U.S. PATENT DOCUMENTS

| | | | |
|---|---|---|---|
| 6,694,285 B1* | 2/2004 | Choe et al. | 702/182 |
| 7,027,953 B2* | 4/2006 | Klein | 702/184 |
| 7,124,637 B2* | 10/2006 | Singhal et al. | 73/659 |
| 7,937,231 B2* | 5/2011 | Janssens et al. | 702/75 |
| 2004/0060347 A1 | 4/2004 | Comperat et al. | |
| 2005/0119840 A1 | 6/2005 | Astley et al. | |
| 2008/0033695 A1* | 2/2008 | Sahara et al. | 702/185 |
| 2008/0223135 A1* | 9/2008 | Blanchard et al. | 73/579 |

* cited by examiner

METHOD AND APPARATUS FOR MONITORING AND ANALYZING VIBRATIONS IN ROTARY MACHINES

The present invention relates to a method and apparatus for monitoring vibrations in machines from which vibration, pressure, or acoustic spectra may be obtained, and in particular to analyzing and monitoring the spectral content of such data to facilitate reliable fault detection.

To monitor the performance and operation of rotary machines it is well known to record and analyze spectra of vibration data obtained using vibration transducers mounted on the machines. The spectral content of vibration data from a rotary machine operating normally tends to be relatively stable and so abnormal operation (such as a developing fault) can be recognised by a change in the spectrum, in particular significant change in the energy at one or more different frequencies. Typically the time-dependent vibration signal from the transducer is transformed into vibration spectra using the Fast Fourier Transform (FFT), resulting in a time-series of spectra. Such spectra may, for example, be generated at a rate of 5 Hz. Typical applications for such monitoring include: gas turbine engines (e.g. aircraft engines), marine engines and large-ship turbochargers, drill-bits and other machines and machine components in manufacturing processes and rotating components in automotive engines.

Figure 1:
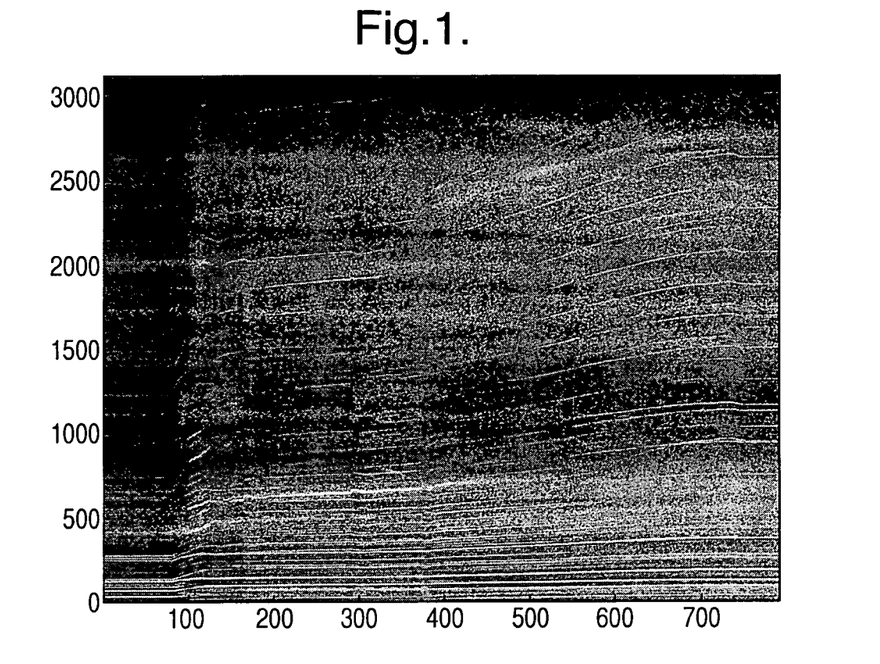
FIG. 1 is a conventional time-frequency plot of vibration spectra against time.

Plotting the vibration spectra against time results in a time-frequency vibration plot and an example of such a plot, in this case for a gas turbine engine, is shown in FIG. 1.

Noting that a FFT contains $N_{FFT}=2^n$ frequency bins covering the frequency range $[0 f_s/2]$, where $f_s$ is the sampling rate of the case-mounted vibration transducer, (for example 10 KH$_z$), a time-frequency plot consists of $N_{FFT}$ rows and t columns, where t is the number of FFTs obtained (e.g. 5 per second for the length of an engine run). Over the duration of a flight, t typically becomes very large meaning that there is a lot of data to handle and the computational burden of processing large quantities of data is high.

Contained within the time-frequency vibration plots are peaks in frequency corresponding to the fundamental and harmonic modes of vibration of the machine. Tracking the amplitude of these peaks, which represent significant spectral components related to resonances of rotary machines, results in time-series called "tracked orders" (TOs), which can be used to characterise the performance of the machine. These "orders", i.e. modes of vibration related to rotation, can be "tracked" through time as they move in frequency space with changes in rotational speed. PCT publication WO-2004/090486 proposed utilising this to construct a model of "normal" behaviour in terms of the tracked orders. Tracked order values from previously-unseen test datasets were then compared with the model of behaviour observed during the training period in order to determine whether or not they are similar to this assumedly "normal" behaviour, or "abnormal", with the goal of identifying abnormal behaviour that indicates system deterioration in advance of system failure.

There are however many modes of failure that cannot be identified by using models of normality constructed using tracked orders. The tracked orders cover only a small sub-range of the entire frequency range of the full vibration spectra, and other modes of failure can result in novel energy (i.e., energy not observed at that part of the frequency spectrum in the training data) appearing outside this small sub-range.

An example of this is the failure of engine bearings in a gas turbine engine. Typically these use small ball-bearings enclosed within fixed cages such that they may rotate freely in order to form load-bearing contacts between the various rotating engine shafts, and to maintain the position of the shafts relative to one another. Damage to the surfaces of these bearings may result in previously-unobserved vibration energy at high frequencies, significantly removed from the narrow frequency bands of the tracked orders observed under "normal" conditions. Failure of the cages in which bearings are mounted can result in constant peaks in spectral energy at previously-unseen multiples of the fundamental tracked orders. The latter could be described as "novel tracked orders" (NTOs) because they are peaks in vibration energy within narrow frequency bands, and are thus tracked orders, but occur at frequencies where tracked orders are not observed under "normal" conditions.

In order to identify NTOs and other significant spectral content not previously observed during training periods of "normal" operation within time-series of spectra, it is necessary to identify and disregard spectral components corresponding to background noise. It has been previously proposed to do this heuristically for all gas turbine engines of a similar class by defining a "noise-floor" threshold on spectral energy (in terms of vibration amplitude), below which spectral components are deemed to be noise. In order to avoid large numbers of false-positive classifications during detection of novel tracked orders when using this threshold with an entire class of engines, it must be set conservatively due to inter-engine variability within that class. However, this causes novelty detection to have low sensitivity, because the conservative threshold results in a high number of false-negative classifications.

The use of this noise floor threshold also results in an inability to determine significant engine events that manifest as changes in spectral energy at frequencies much higher than the first few harmonics of fundamental tracked orders, which may be an indication of bearing distress, bearing failure, and other events occurring at higher frequencies, because these tend to have a much lower amplitude than vibration at lower frequencies.

According to the present invention there is provided a method of monitoring vibration amplitude and frequency in a rotary machine, comprising the steps of:—
  receiving measurements of the amplitude and frequency of vibrations and the rotation speed of the machine;
  recording as a data point each amplitude measurement as a function of vibration frequency and rotational speed;
  storing a plurality of different amplitude thresholds each representing a noise floor for a respective one of a first set of sub-ranges of vibration frequency and rotational speed;
  comparing each amplitude measurement to the amplitude threshold for the sub-range of vibration frequency and rotational speed within which it falls; and
  determining the measurement as representing noise if it falls below the threshold and as significant spectral content if it is above the threshold.

Thus with the present invention the vibration amplitudes are recorded as a function of frequency and the rotation speed of the machine, rather than frequency and time. This is a particularly good way to characterise the behaviour of rotary machines as their vibration spectra typically vary as a (non-linear) function of rotation speed.

The invention also stores a different noise floor threshold for each of a plurality of sub-ranges of frequency and rotational speed. In one example the whole frequency range can be divided into between 50 and 100 sub-ranges or "bins", and the entire rotational speed range, expressed as a percentage of maximum speed, can be divided into 20 to 40 sub-ranges or "bins", and an amplitude threshold representing the noise floor can be stored for each speed-frequency bin (i.e. each different combination of a frequency sub-range with a speed sub-range). This use of different noise floor thresholds is essential because the amplitude of noise decreases nonlinearly with increasing frequency. This allows an appropriate noise floor to be set for each of the speed-frequency bins meaning that at high frequencies the noise floor can be set lower than the noise floor at lower frequencies which allows significant spectral content at higher frequencies, such as tracked orders corresponding to higher harmonics, to be detected and monitored rather than being lost beneath a noise floor appropriate to lower frequencies.

Preferably the different noise floors for the different speed-frequency bins are set in a training process using training data points consisting of vibration data from one or more runs of the rotary machine that has been deemed to be "normal". Thus the training data in each speed-frequency bin can be analyzed and a suitable noise floor threshold can be set.

Preferably this analysis comprises fitting an amplitude distribution to the training data points in the speed-frequency bin, then calculating an extreme value distribution (EVD) from the fitted amplitude distribution, and then choosing as the noise floor threshold an amplitude value which represents a particular probability of being an extremum for a data set with that amplitude distribution. For example, using this technique it is possible to find the amplitude which has a 99% probability of being the highest value in any given set of points drawn randomly from that distribution, and to set this value as the noise floor threshold. Different probabilities can be chosen to set the threshold if desired, in order to characterise noise levels from systems with differing noise characteristics.

In one example, applied to a gas turbine engine, the distribution of amplitudes in each speed-frequency bin is a Gamma distribution and thus the extreme value distribution is a Gumbel distribution.

Preferably the amplitude distribution is fitted to the training data points after excluding any data points which represent significant spectral content, e.g. tracked orders. This can be achieved by first fitting an amplitude distribution to all of the training data points within the speed-frequency bin, then excluding outlying data points, e.g. defined as those which are more than three standard deviations from the mean of the first fitted distribution. The trimmed data set without the excluded data points is then used to fit the amplitude distribution again, and the EVD is calculated from the re-fitted amplitude distribution. This allows the EVD to be based only on the data representing background noise, not the significant spectral content appearing above the resultant noise-floor (which may be tracked orders, novel tracked orders, or other significant spectral content).

The number and positioning of the sub-ranges of frequency and rotational speed (referred to as speed-frequency bins) are preferably set in a training process such that a sufficient amount of training data is included in each speed-frequency bin.

Having obtained an extreme value distribution (EVD) for each of the speed-frequency bins, which gives the probability that any given vibration amplitude is the likely maximum amplitude value that would be obtained for noise for a data set drawn from that distribution, one embodiment of the invention utilises this to allow calculation of a novelty value defined as $-\log_{10}\{1-P_e(x)\}$. This novelty value is particularly effective when displayed in enhancing the visualisation of the significant spectral content, e.g. tracked orders and eliminating data which corresponds to background noise, rather than viewing the original time-series of spectra. In the latter, significant spectral content of interest may be barely visible (particularly at higher frequencies) because it is similar in amplitude to the noise at lower frequencies. By viewing the novelty values, such low-amplitude significant spectral content is emphasised, while background noise is attenuated An embodiment of the invention also allows the detection and monitoring of novel significant spectral content not present during normal operation of the machine (more accurately not present in the training data). These may be higher harmonics of the fundamental tracked orders, or spectral content unrelated to any tracked order contained in the training data.

This can be achieved by defining during a training process which speed-frequency bins correspond to known tracked orders, and thus which speed-frequency bins do not have any tracked orders in them during "normal" operation. Then if, during operation of the machine, significant vibration amplitude appears in a speed-frequency bin other than one of those that contain known tracked orders, this can be regarded as novel significant spectral content and be displayed as a new feature and/or form the basis of an alert. By significant vibration amplitude, we mean a vibration amplitude above the noise floor appropriate for that speed and frequency. It may be that the alert can appear on the basis of one data point appearing as novel significant spectral content (e.g. novel tracked order), i.e. one FFT containing such novel data, or it may be that a pre-set number of data points, optionally in succession or at least close in time, are required before it is regarded as novel significant spectral content.

It should be noted that the size and number of the speed-frequency bins for detection of known tracked orders and novel significant spectral content need not be the same as the size and positioning of the speed-frequency bin used for the noise floor calculation. It is possible for the speed-frequency bins for detecting known tracked order and novel significant spectral content to be larger or smaller than the speed-frequency bins used for noise floor calculation.

Preferably known tracked orders are defined as speed-frequency bins which include more than a pre-set number of vibration amplitude data points above the noise floor in a training data set representing "normal" operation of the machine (i.e., normally having significant spectral content above the background noise). The pre-set number of significant data, and also the number and size of the speed-frequency bins, can be set by comparing the behaviour of the method on a normal data set and on an abnormal data set (i.e., a data set containing data points known to be indicative of "abnormal" behaviour). By setting the pre-set number of significant data and the number and size of bins appropriately only those bins which contain the abnormal data points will be regarded as novel significant spectral content.

The invention extends to an apparatus for monitoring the vibration amplitude and frequency of a rotary machine, the apparatus operating in accordance with the method described above. Such apparatus may be part of a control system for the rotary machine.

The method may be embodied in software executable on a computer or other system having data processing capability.

The invention will be further described by way of examples with reference to the accompanying drawings in which:—

FIG. 12 (a) to (d) illustrate the effects on sensitivity of different quantisations of speed-frequency space;

FIGS. 13 (a) and (b) illustrate the vibration data and the detection according to one embodiment of the invention of novel significant spectral content representative of bearing cage failure in a gas turbine engine; and FIGS. 14 (a) and (b) illustrate the vibration data and the detection according to one embodiment of the invention of novel significant spectral content representative of bearing damage in a gas turbine engine.

Figure 2:
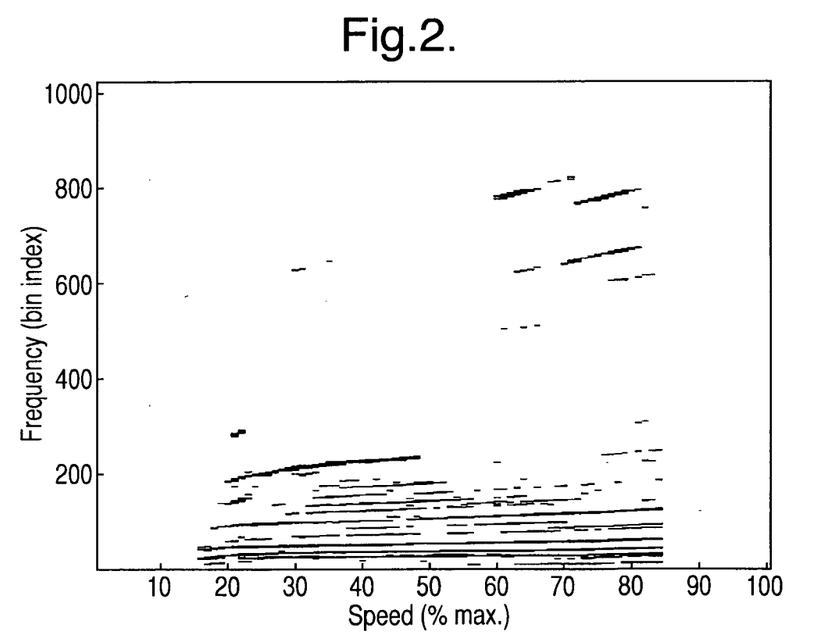
FIG. 2 illustrates a speed-based representation of spectral vibration data according to one embodiment of the invention.

FIG. 2 illustrates a speed-based representation of spectral vibration data in accordance with an embodiment of the invention in which the amplitude measurements from the vibration sensor are recorded as a function of vibration frequency and rotational speed. In FIG. 2 the mean vibration amplitude in each of the $f_i$ $i=1 \ldots N_{FFT}$ spectral bins (here, $N_{FFT}=1024$), collected in 1% sub-ranges of shaft speed $w_{LP}$, from a run of a gas turbine engine during a single flight is plotted, with the mean vibration amplitude being represented by the grey level of the plotted data point with higher amplitudes being closer to black. This illustration also shows the speed-frequency space being divided into 10×10 speed-frequency sub-ranges or bins.

Energy associated with the fundamental tracked orders appears in the lowest decile of the frequency range, from shaft speeds between 15% and 85% of maximum (noting that the engine is idle when $w_{LP}<30\%$). Energy associated with the second harmonic tracked orders appears in the second decile of the frequency range (though at lower amplitudes than the fundamental tracked orders), while a single high-energy harmonic can be seen around spectral bin $f_{220}$ between 20% and 50% shaft speed. Low-amplitude energy may be seen occurring between 60% and 80% shaft speed, between spectral bins $f_{600}$ and $f_{500}$.

Recording the spectral data as a function of speed effectively compresses the information making it easier to analyse and visualise. Also as vibration amplitude is a nonlinear function of speed and frequency this nonlinear function is modelled using probabilistic distributions, such that "normal" behaviour can be characterised and thus allowing detection of "abnormal" behaviour.

Figure 3:
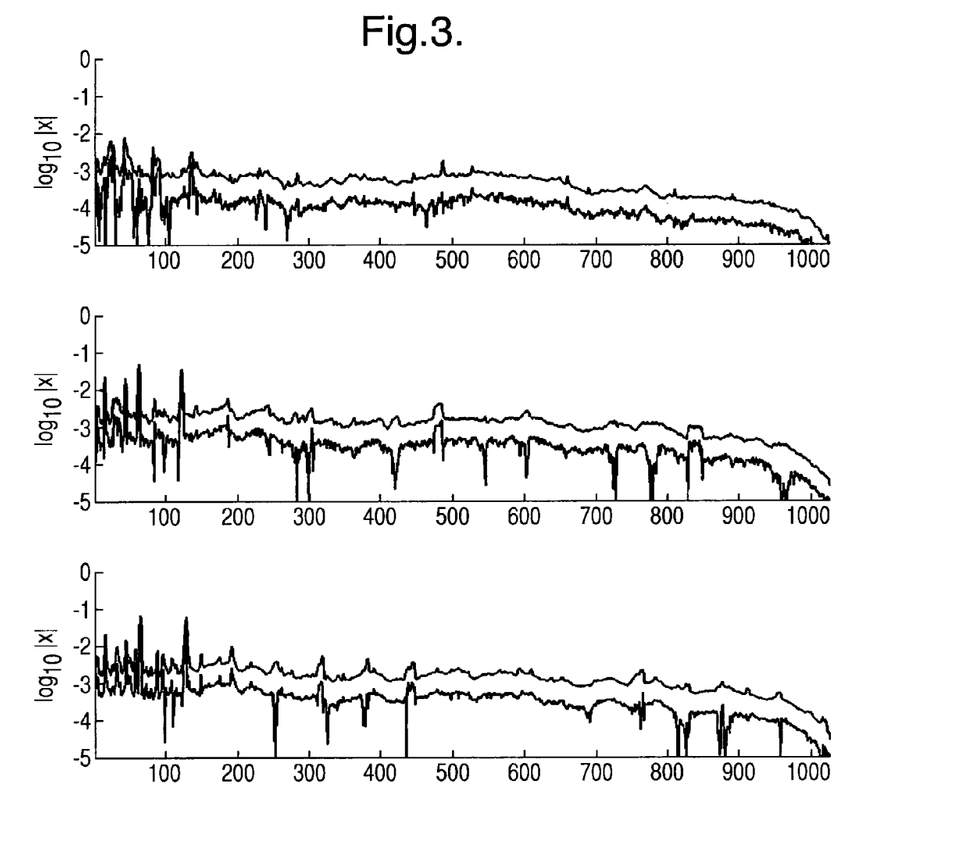
FIG. 3 is a log and plot of vibration amplitude against frequency.

As discussed above, analysing vibration data by means of tracked orders is effective at lower frequencies but difficult at high frequencies because the tracked orders take similar vibration amplitudes to that of noise. FIG. 3 shows a plot of $-\log_{10}$ of vibration amplitude against frequency and log of log plots across the whole frequency range for low pressure shaft speed of 30%, 60% and 90% in a gas turbine engine. Tracked orders can be seen as spikes in the amplitude with the remainder being noise, but it can be seen that there is no relationship between noise amplitude and frequency which would allow noise to be treated using a conventional simple linear or polynomial function. In accordance with an embodiment of the present invention a set of training data is taken and divided up into speed-frequency sub ranges or bins, and a noise floor is calculated for each of the bins. How this is done will be explained below.

In the case of an aircraft engine (but the same phenomenon also occurs in other machinery) the engine spends most of the time operating at either idle or cruising speed, with relatively short periods of other speeds corresponding to climbing, landing or other manoeuvres. This means that there is a lot of data for the idling and cruising engine speeds and a relatively small amount of data for other engine speeds. Therefore the size of the speed-frequency bins used for calculating the noise floor needs to be chosen so that there is a statistically significant amount of data in each bin. Clearly this depends on the size and nature of the data set under consideration. In the example described below, using gas turbine vibration data collected during several aircraft flights, the division of the speed range into 20 sub-ranges and the frequency range into 100 sub ranges, thus providing 20×100 bins, provided at least 100 data points in each bin giving a suitable compromise between retaining a fine quantisation of the speed-frequency space with sufficient data to calculate the noise floor. (Each data point has three components being: the amplitude and frequency of one of the 1024 components of the FFT, together with the LP (low pressure) shaft speed at that time.)

Figure 4:
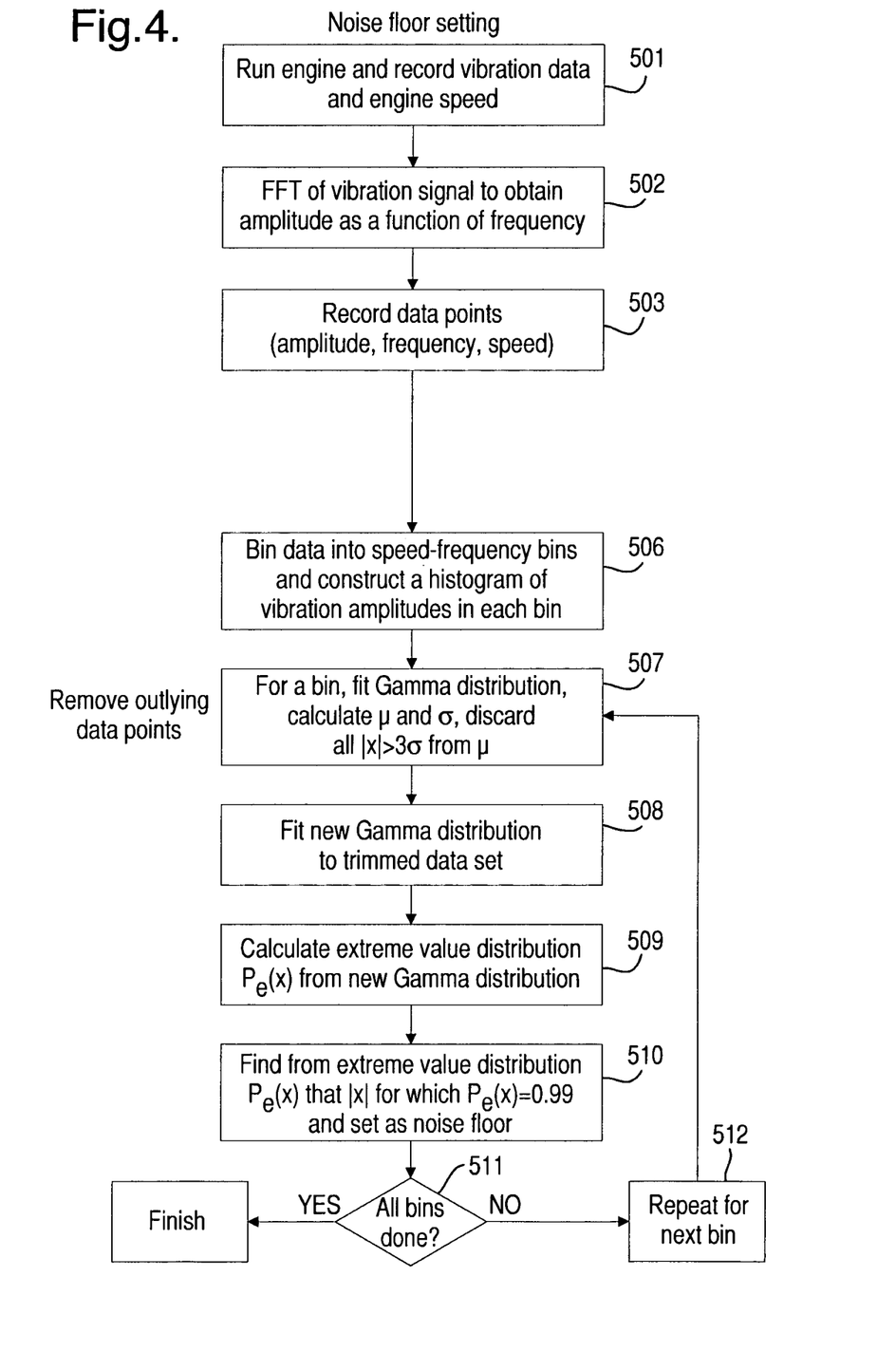
FIG. 4 is a flow chart explaining noise floor setting in relation to vibration data according to one embodiment of the invention.
Figure 5A:
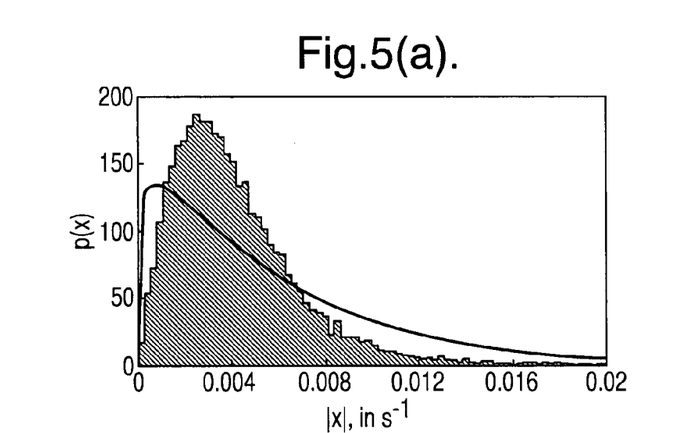
FIGS. 5(a) to (c) illustrate parts of a histogram of vibration data and fits of a Gamma distribution.
Figure 5B:
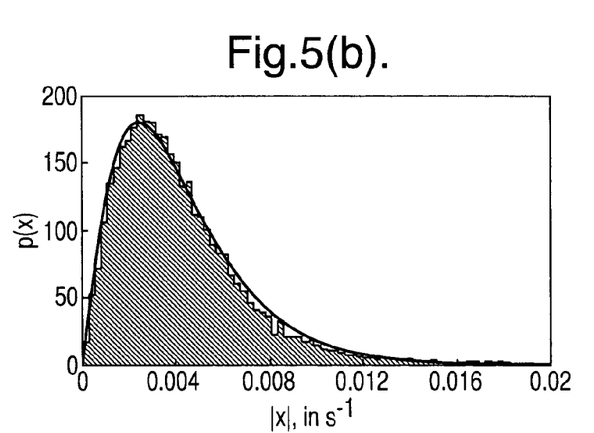
Figure 5C:
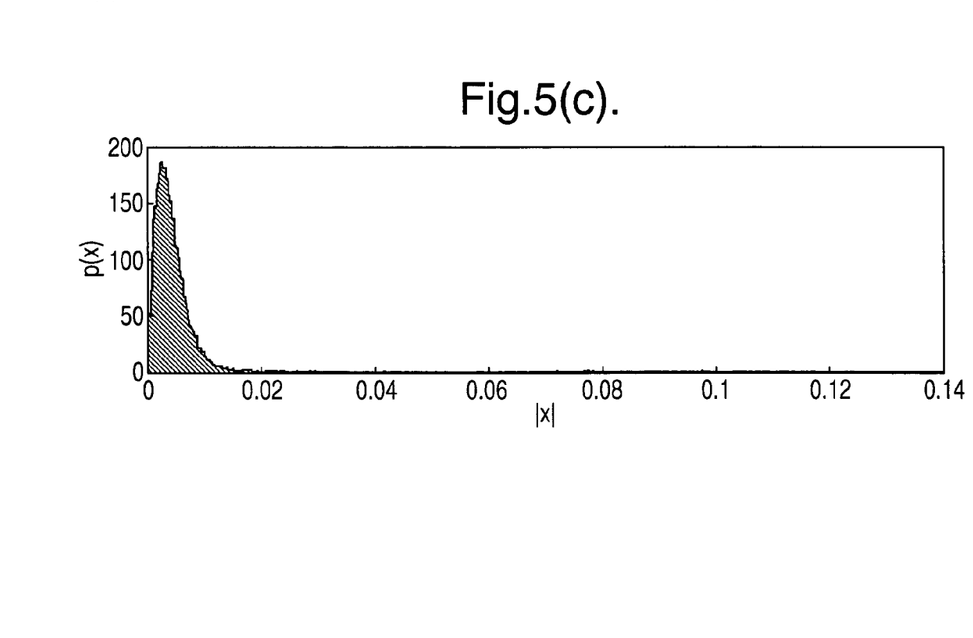

How the noise floors are set for each of the 20×100 speed-frequency bins will now be described with reference to the flowchart of FIG. 4. The noise floor is set with reference to a set of training data obtained by running the engine (or other rotary machine) and recording the vibration data and engine speed as shown in step 501. As well-known in the art of spectral analysis the vibration data is subject to a Fast Fourier Transform in step 502 so that in step 503 a set of training data consisting of training data points each having the three components of vibration amplitude, frequency and rotational speed are obtained. For obtaining the noise floor a training data set representative of normal operation is required. Using such a normal training data set the data points are binned into their respective speed-frequency bins in step 506, and for each of the 20×100 bins a histogram is constructed to show the distribution of amplitudes within that speed-frequency bin. FIG. 5 illustrates part of such a histogram, in this case for speed bin 16, frequency bin 5 of a training data set which happened to contain energy associated with a tracked order vibration which is not visible in FIGS. 5 (a) and (b) as it is an order of magnitude higher on the x-axis than the data illustrated— i.e. significantly far off the right-hand side of the illustration at the scale shown in FIG. 5(a). This can be seen in FIG. 5(c), in which tracked order vibration occurs up to x=0.14 inches per second. Note that the number of data corresponding to tracked order vibration is low with respect to the number of data corresponding to noise. Thus in FIG. 5 each column of the histogram represents the number of data samples in bin $b_\omega$=16, $b_f$=5 with that vibration amplitude. A similar histogram is constructed for each of the 20×100 speed-frequency bins forming the speed-frequency space for this data set.

The shape of the histogram corresponds to that of a Gamma distribution, meaning that the Gamma distribution is a suitable model for this data. The aim, however, is to model in particular the noise in each speed-frequency bin, rather than the tracked orders which are significant spectral components of interest. It can be seen from FIG. 5(a) that fitting a Gamma distribution to all of the data in a bin containing a tracked order does not give a particularly good fit (the Gamma distribution is the solid line) because of the significant amplitude in the tracked orders well to the right of the illustration, as shown in FIG. 5(c), which skews the distribution away from fitting the main (Gamma) distribution of the noise amplitudes. Therefore in step 507 of the method a trimmed data set is produced by excluding the data points corresponding to the tracked orders in that bin. This can be achieved by fitting an initial ML (Maximum Likelihood) Gamma distribution to all of the data in the bin (as illustrated in FIG. 5(a)), and calculating the mean and standard deviation of the fitted Gamma distribution. Then any data points which lie more than three standard deviations from this mean are excluded and a new fit of an ML Gamma distribution is conducted with the remaining data in step 508. The result of this is illustrated in FIG. 5(b) and it can be seen that the fit is much better to this data representing noise.

Figure 6:
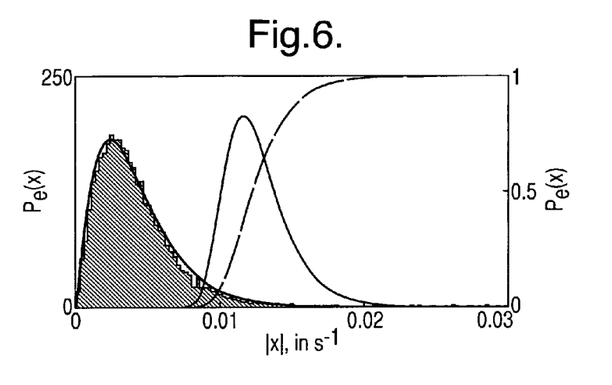
FIG. 6 illustrates Gamma and Gumbel and cumulative Gumbel fits to the histogram of FIG. 5 according to one embodiment of the invention.

In order to set an appropriate noise floor (amplitude threshold) below which the data will be regarded as noise, this embodiment uses extreme value statistics in order to model more accurately the tail of the Gamma distribution where there is less data. Bearing in mind that the noise in each bin is being modelled by a Gamma distribution, the aim is to determine the highest amplitude value which would still be regarded as noise (i.e. which would be generated from the Gamma distribution for that bin). An extreme value distribution (EVD) can be used to indicate what is the likely maximum amplitude value that would be obtained for noise. The extreme value distribution calculated from the Gamma distribution for the histogram of FIG. 5 is illustrated in FIG. 6. The line $p_e(x)$ is the distribution of extreme values which is a classical Gumbel EVD. The line $P_e(x)$ illustrates the cumulative probability calculated from the classical Gumbel EVD. Thus by referring to the right-hand vertical axis of FIG. 6 and the cumulative Gumbel $P_e(x)$ it is possible to find which amplitude value has any desired probability of being the extreme value of data with this distribution.

Figure 7A:
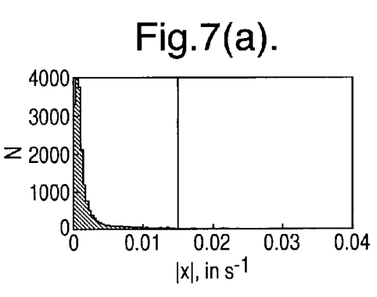
FIGS. 7(a) to (d) illustrates noise floor setting to two different speed-frequency bins according to one embodiment of the invention.
Figure 7B:
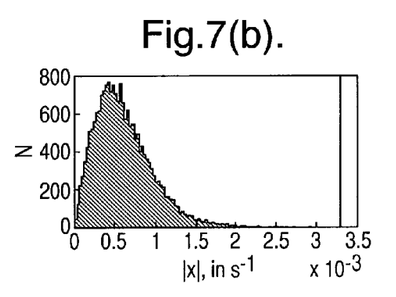
Figure 7C:
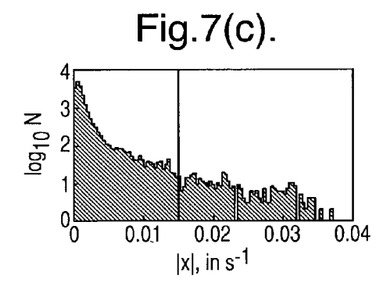
Figure 7D:
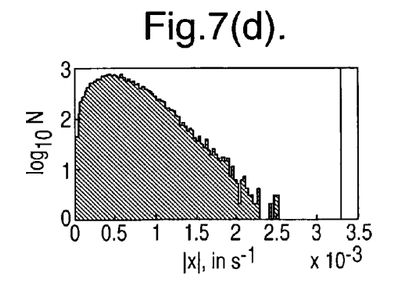

Thus step 509 of the method involves calculating the vibration amplitude value corresponding to the desired probability for the noise floor. FIGS. 7(a) to (d) illustrate the noise floor threshold set for each of two speed-frequency bins with the threshold set as the vibration amplitude having probability $P_e(x)$=0.99 of the cumulative Gumbel for that bin. FIG. 7(a) is the data from a speed bin 8, frequency bin 5 which contains a tracked order whereas FIG. 7(b) illustrates the data for speed bin 8, frequency bin 40 which does not contain a tracked order. It should be noted that the vibration amplitudes on the horizontal axis of FIG. 7(b) are an order of magnitude lower than those on FIG. 7(a) (because this bin contains no tracked order). FIGS. 7(c) and 7(d) show the same data using $\log_{10}$y-axis which allow it to be seen that the tail of the distribution and vibration amplitudes for the bin containing tracked order energy of FIG. 7(c) extends well above the noise floor threshold, while the distribution for the window containing no tracked order energy, shown in FIG. 7(d), does not and so all data in that bin is deemed background noise. The noise floor thresholds marked in FIG. 7 are at 0.014 inches per second for the tracked order bin and 0.0033 inches per second for the non tracked order bin.

This process is repeated by step 511 and in this way a noise floor threshold is set for each of the bins representing a sub-range of frequency and speed in the speed-frequency space.

Figure 8:
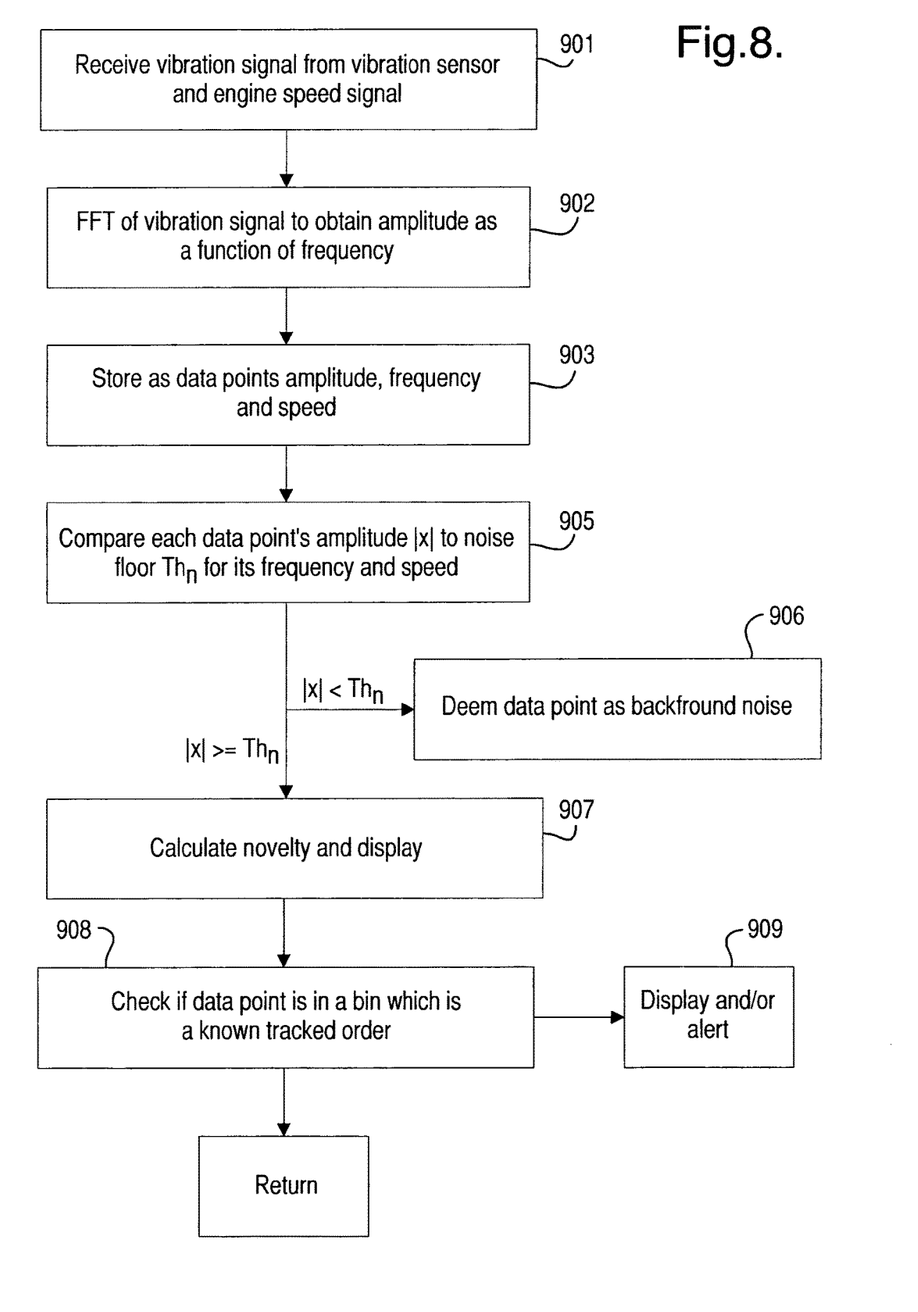
FIG. 8 is a flow chart explaining monitoring of vibration data according to one embodiment of the invention.

Having set a noise floor amplitude threshold for each part of the speed-frequency space these may be used when monitoring engine performance in determining whether each incoming sample of vibration data represents noise or a significant spectral component such as a tracked order, novel tracked order, or other significant spectral content. FIG. 8 illustrates such a monitoring process. In step 901 vibration data from a vibration sensor and an engine speed signal are received and in step 902 the vibration data is Fast Fourier Transformed to obtain the vibration amplitude as a function of frequency. In step 903 each amplitude measurement is then stored as a data point as a function of frequency and engine LP shaft speed. For each data point its vibration amplitude is then compared in step 905 to the appropriate noise floor for the speed-frequency sub range (bin) into which it falls. If the vibration amplitude is less than the noise floor it can be deemed noise in step 906, but if it is greater than or equal to the threshold it represents significant spectral content.

Figure 9:
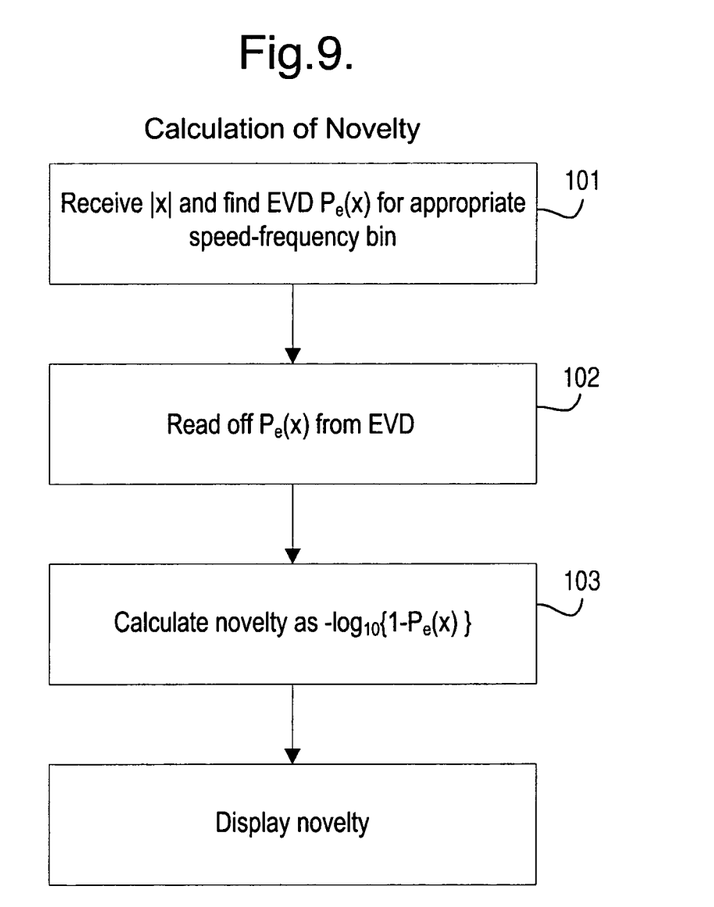
FIG. 9 is a flow chart explaining novelty value calculation according to one embodiment of the invention.

In this embodiment for each data point representing an observed vibration amplitude a "novelty score" is calculated and displayed in step 907. FIG. 9 illustrates how the novelty score is calculated. The novelty score z(x) is a quantity that increases with the probability that x is not noise; i.e., that x corresponds to significant spectral content. One example of such an index may defined as:—

$$z(x)=-\log_{10}\{1-P_e(x)\}$$

Thus for each data point the vibration amplitude x is compared to the cumulative EVD $P_e(x)$ (of which one is illustrated in FIG. 6) to read off in step 102 the corresponding probability $P_e(x)$ that the extreme value is lower than this The novelty score is then calculated from this probability value using the formula above. FIG. 10 illustrates the relationship between the vibration amplitude, probability $P_e(x)$, and novelty z(x) for spectral data at time T=680 for the training data used previously.

Figure 10A:
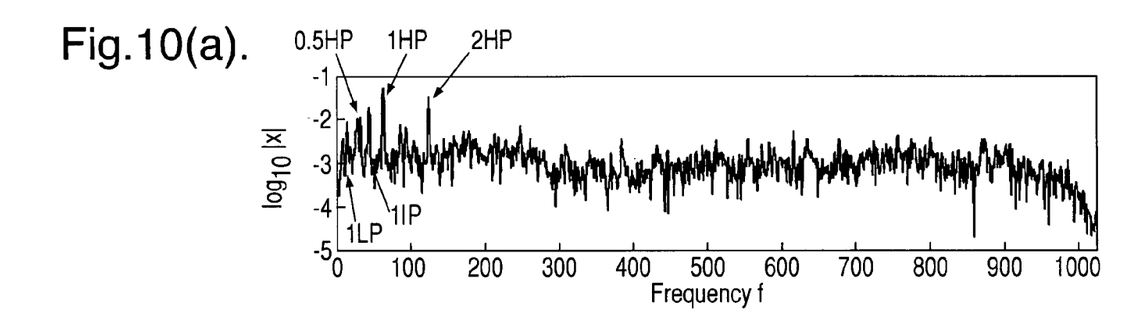
FIGS. 10(a) to (c) illustrate log vibration amplitude, and corresponding probability and novelty values calculated for one temporal sample of vibration data according to one embodiment of the invention.
Figure 10B:
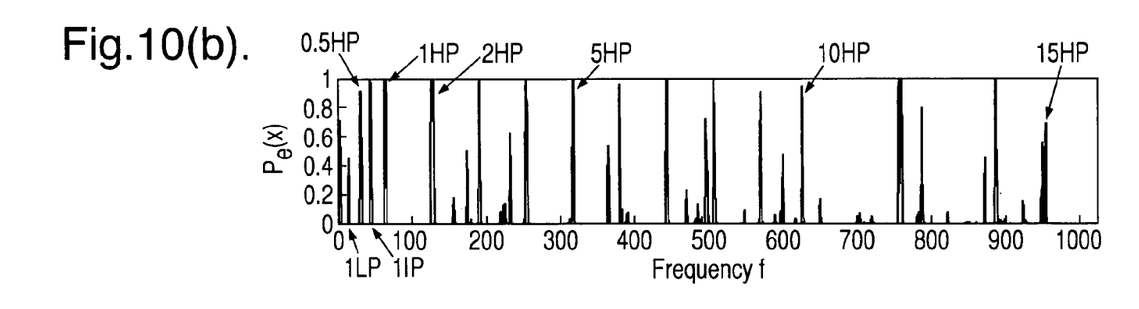
Figure 10C:
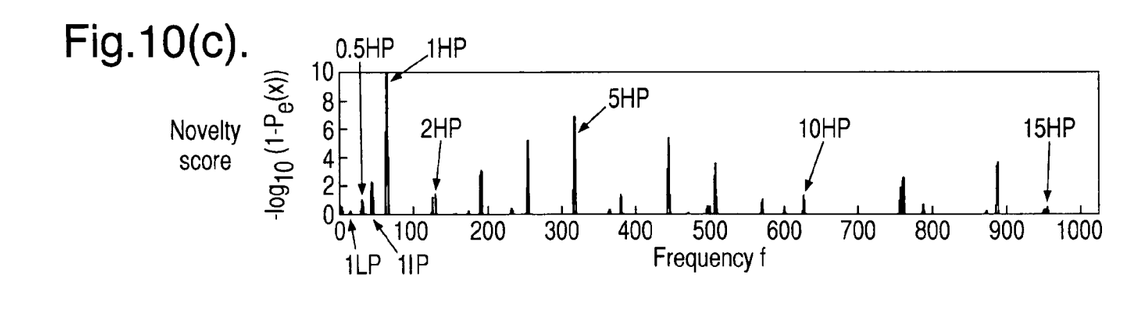

FIG. 10(a) illustrates the log amplitude and it can be seen that only the fundamentals from the low pressure, intermediate pressure and high pressure shafts can be seen together with two harmonics of the high pressure shaft. No significant spectral content can be distinguished in the majority of the frequency range extending from component $f_{120}$ to $f_{1024}$ FIG. 10(b) shows the probabilities calculated in the manner described above, thus using different noise floors for the different frequency bins and the cumulative EVD. FIG. 10(c) shows the corresponding novelty scores z(x) calculated in accordance with the formula above. It can be seen that it is possible to identify higher-order harmonic tracked orders throughout the frequency range because they have probability and novelty values much greater than those of the surrounding spectral components containing background noise. It can be seen that even the 15$^{th}$ harmonic of the high pressure shaft can be seen relatively easily occurring at spectral component $f_{950}$.

Thus using this method spectral information content not previously available can be extracted from the vibration data. This allows better analysis and monitoring of the machine performance, making use of information that was not available using existing techniques.

It was mentioned above that current proposals of spectral analysis of vibration data focus on monitoring the known tracked orders. However some modes of failure manifest themselves in the sudden appearance of energy at frequencies where no significant spectral content has been observed before. Building on the analysis above this embodiment of the invention allows such novel significant spectral content to be detected efficiently. In order to achieve this the location of significant spectral content observed during the training period is first recorded by observation of training data from one or more runs of the machine which have been deemed to be normal. This gives a model of normality.

An example based on the same data for a gas turbine engine as used above will now be described.

Figure 11:
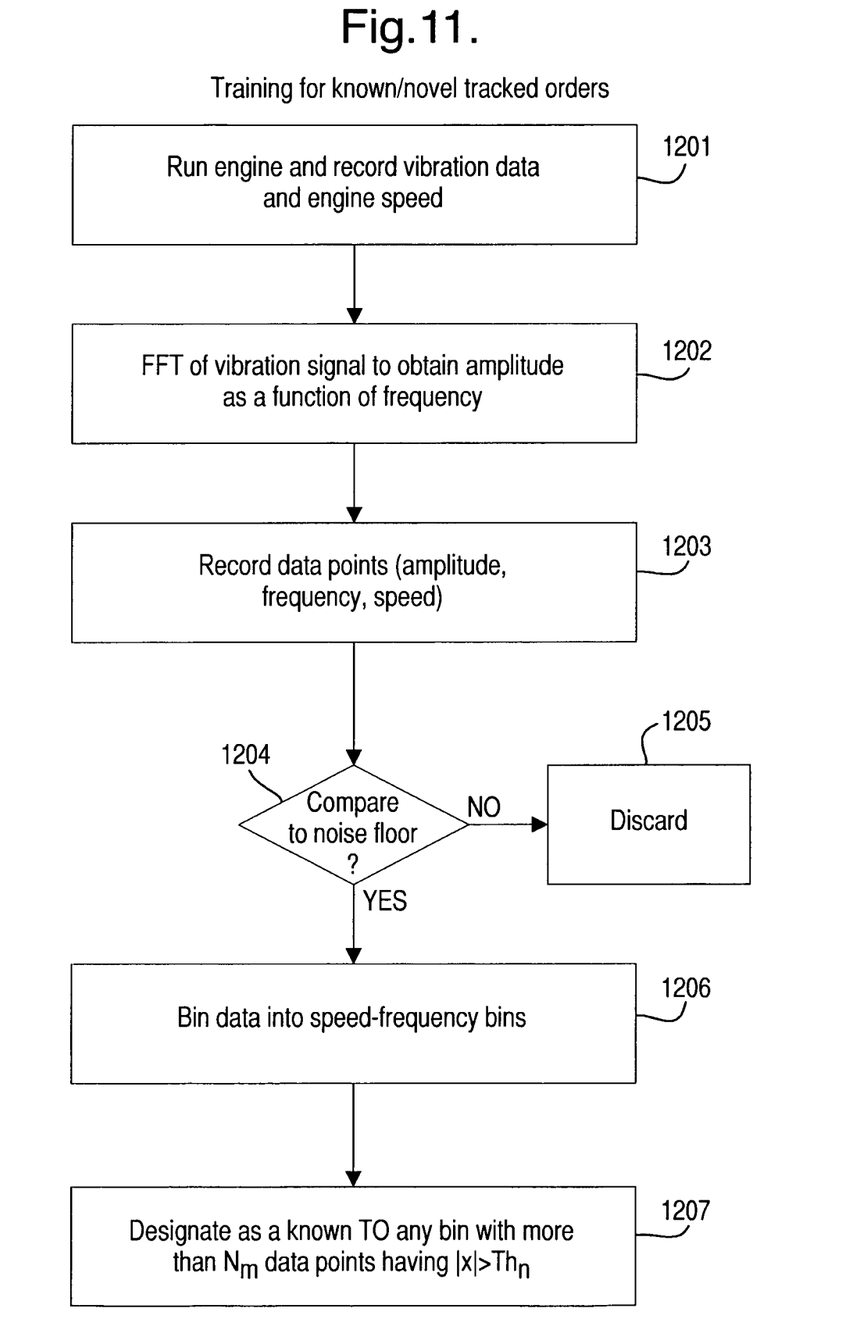
FIG. 11 is a flow chart explaining training of the model for known tracked order and novel significant spectral content according to one embodiment of the invention.

As illustrated in FIG. 11 the training data from a normal engine run (or more than one run) is obtained in step 1201. As before this data is Fast Fourier Transformed in step 1202 to obtain in step 1203 data points with the three values of amplitude, frequency and engine speed. In step 1204, any data points with vibration amplitudes deemed to be background noise (i.e. below the appropriate noise floor threshold described above) are discarded in step 1205. The remaining data is then binned into speed-frequency bins in step 1206. It should be noted that the speed-frequency bins for step 1206 can be the same as the speed-frequency bins used for definition of the noise floor in step 506. However, they can instead be different. How to decide the number of bins will be described below.

Assuming that there are $N'_{b\omega} \times N'_{bf}$ speed-frequency bins, a counting matrix $C_{ij}$ can be defined such that element (i,j) is set to the number of samples (above the noise floor) in the training set that fall within the corresponding speed-frequency bin (i,j). Any bin corresponding to the speed and frequency of a fundamental or lower-order harmonic tracked order will result in large numbers of data falling in bins in the lower part of the frequency range, while higher-order harmonics result in larger counts in the higher parts of the frequency range. Most bins will have no samples at all. Thus the C matrix characterises the distribution of significant spectral content throughout the speed-frequency space for the training data. Bearing in mind that bins corresponding to tracked orders will contain high numbers of samples, a number $N_m$ is defined so that any bin (i,j) with $C_{ij}$ greater than or equal to $N_m$ is considered to contain "known significant spectral content". This will mean that when real data is analysed during operation of an engine, any sample above the noise floor and falling into a bin for which $C_{ij}$ is greater or equal to $N_m$ will be regarded as known significant spectral content. Conversely any sample above the noise floor which falls into a bin for which $C_{ij}$ is less than $N_m$ will be regarded as novel significant spectral content because the training set did not contain a significant ($N_m$) number of samples above the noise floor in that bin.

This monitoring of real data is illustrated in steps 908 and 909 of FIG. 8 in which each sample above the noise floor appropriate to its frequency and speed is checked in step 908 to see whether it is in a speed-frequency bin which has been designated as known significant spectral content (in the training process). If not then the sample is representative of novel significant spectral content and this can be displayed at step 909 and an alarm triggered if necessary. In addition, the alarm condition can be triggered if a threshold number of samples representing novel significant spectral content are found, or if novel significant spectral content persists for a certain time.

Figure 12A:
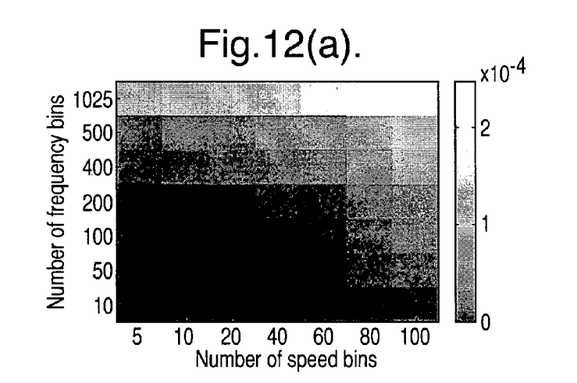
Figure 12B:
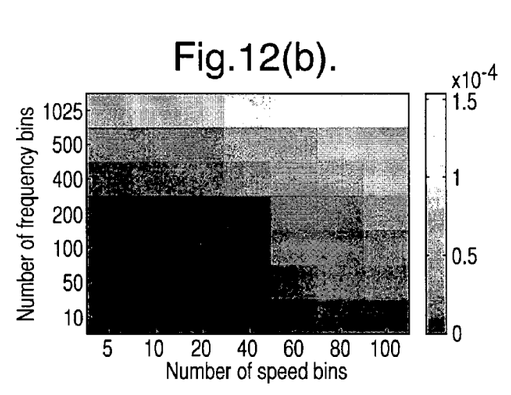
Figure 12C:
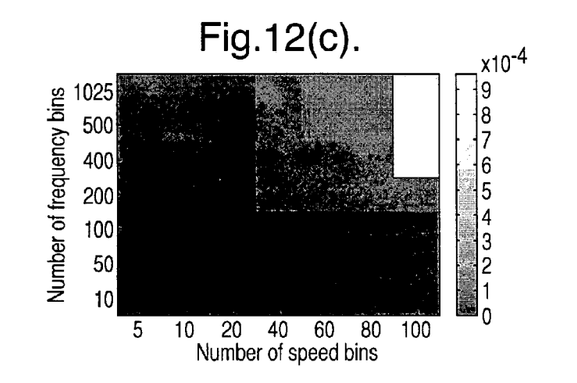
Figure 12D:
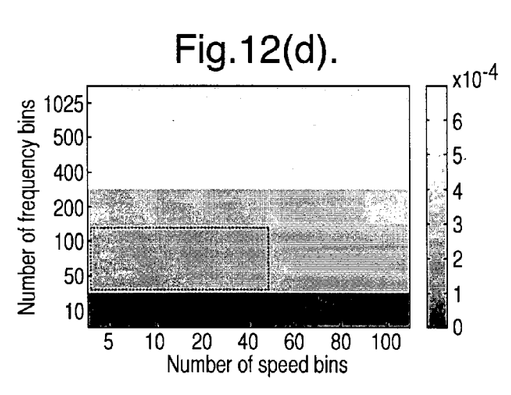

It will be appreciated that the level of quantisation of the speed-frequency space (i.e. the number of speed-frequency bins), and also the selection of the threshold $N_m$ affect the sensitivity of the method. If the number of bins is small (i.e. coarse quantisation of the speed-frequency space) and $N_m$ is also small then a high proportion of the bins will contain known significant spectral content with respect to the training data. Thus the method will be relatively insensitive and the method will be subject to many false negatives. On the other hand if the quantisation of speed-frequency space is too fine, so that there are many speed-frequency bins, and/or $N_m$ is large, then a relatively small proportion of the bins will be regarded as containing known significant spectral content in relation to the training date, so when monitoring new data it is much more likely that a new data sample will fall in a bin not regarded as known significant spectral content, and thus will be classified as novel significant spectral content. This will tend to make the method over-sensitive and generate large numbers of false positives. The values $N'_{b\omega}$, $N'_{bf}$ and $N_m$ can be set appropriately by using training data sets with normal data and training data sets known to contain examples of abnormal engine operation. FIG. 12 illustrates the results of the detection of novel significant spectral content for four data sets, three of which were deemed normal and one abnormal for different quantisation levels of the speed-frequency space. Each plot shows the proportion of spectral data from the data set that is classified as "novel" (i.e. corresponding to novel significant spectral content) for each of 49 different candidate speed-frequency space quantisations (namely $N'_{b\omega}$=5, 10, 20, 40, 60, 80, 100) and $N'_{bf}$=10, 50, 100, 200, 400, 500, 1024, in this case with $N_m$=3. As FIGS. 12(a), (b) and (c) contain data corresponding to normal running of the engine, any "novel" classifications (i.e. non-black areas) correspond to false positives. On the other hand in FIG. 12(d) the data is known to contain novel significant spectral content so any quantisations which result in no novel identifications (black areas) are false negatives. The dotted area in FIG. 12(d) indicates quantisations which correctly identify novel significant spectral content in the data without misclassifying known significant spectral content. Comparing this dotted area to the desired black areas in FIGS. 12(a)-(c) show that quantisations of the frequency range from about 30 to 120 bins and quantisations of the speed range from about 5 to 30 give the correct distinction between novel and known significant spectral content, in this case with $N_m$=3. The same data was used to test the effect of varying $N_m$ and it was found that with $N_m$ greater than 3 the number of false positive novel classifications increases, while with $N_m$ decreasing to 1, no novel classifications were made even in the data of FIG. 12(d). Different values of $N_m$ may be found to be appropriate for different machines.

Figure 13A:
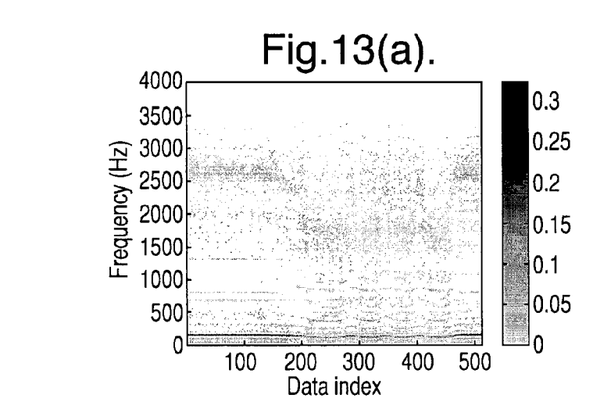
Figure 13B:
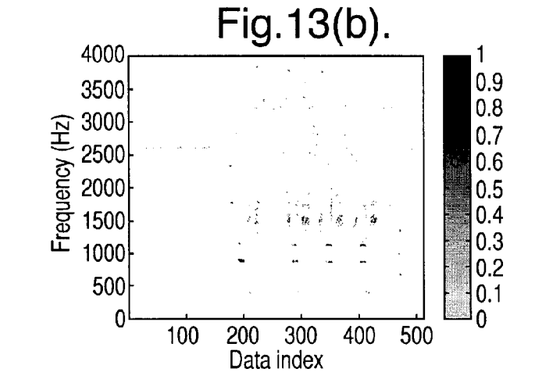

By repeating this testing process on other data sets known to be normal and other data sets known to be abnormal, the optimal quantization of speed-frequency space and setting of $N_m$ can be achieved. It was found that with other data sets from the same gas turbine engine as used above having less than 40 speed bins and 50 or 100 frequency bins, together with $N_m$ about 3 gives good performance. FIG. 13 illustrates the results of applying this detection of novel significant spectral content to different gas turbine engine data. FIG. 13(a) illustrates the complete vibration spectra while FIG. 13(b) illustrates the value of $P_e(x)$ for data points classified as a novel tracked order. That is to say this shows only those data points which are above the noise floor and fall into a speed-frequency bin which was not designated during the training process above as containing known significant spectral content. This shows the high amplitude vibration energy at frequencies corresponding to a bearing cage failure—namely a series of novel tracked orders occurring between T=200 and T=400. In this case $N'_{b\omega}$=20, $N'_{bf}$=100 and $N_m$=3.

Figure 14A:
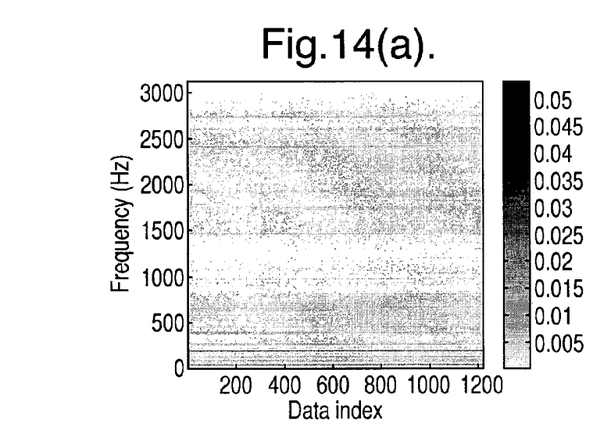
Figure 14B:
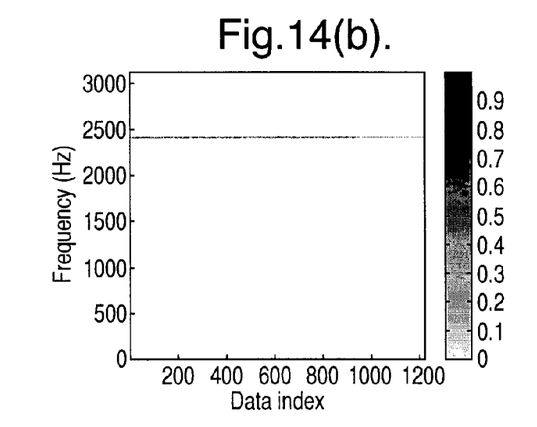

FIG. 14 illustrates the application of the technique to another data set containing abnormal data, with FIG. 14(a) illustrating the whole vibration spectra and FIG. 14(b) illustrating only those data points classified as corresponding to novel significant spectral content. In this case only one novel tracked order corresponding to bearing damage at frequency 2,500 Hz is identified (correctly).

Thus with this aspect of the technique once a noise floor has been set appropriately for each area of speed-frequency space, training data can be used to identify which speed-frequency regions correspond to known significant spectral content by designating as known significant spectral content any speed-frequency bin which contains more than a preset number of samples above the noise floor. During monitoring new data samples which are above the noise floor can then be checked to see whether they fall into a speed-frequency bin designated as known significant spectral content, and if not can be regarded as novel significant spectral content.

SUMMARY

With the technique described above, therefore, a speed-frequency representation of the spectral data is used to characterise the distribution of spectral energy and a noise floor is estimated based on a training data set for each different area (bin) of the speed-frequency space. This allows the detection of higher order harmonic tracked orders which cannot readily be detected with existing techniques. Further, the technique allows a model of normality to be learned from a training set, in terms of the known significant spectral content present in the training data, and then novel significant spectral content can be detected during monitoring of real data. The processes are automatic and thus can be applied to each specific engine or other machine, rather than having to be tuned by expert analysis with respect to a class of engine or machine.

It should also be noted that although the description above is based on the use of designated training data sets, it is possible to re-train the model at any point, or on a continuous basis, based on real data which is regarded as normal. Thus in use of the technique for monitoring an engine or other machine, any run which is normal can be utilised to refine the noise floor estimates and to refine the detection of known significant spectral content.

The invention claimed is:

1. A method of monitoring vibration amplitude and frequency in a rotary machine, comprising:
  receiving measurements of vibration amplitude and rotation speed of the machine from at least one sensor;
  recording as a data point each amplitude measurement as a function of vibration frequency and rotational speed;
  storing a plurality of different amplitude thresholds each representing a noise floor for a respective one of a first set of sub-ranges of vibration frequency and rotational speed,
  wherein each sub-range includes a sub-range of speeds and a sub-range of frequencies,
  wherein the different amplitude thresholds are set in a training process using training data points comprising vibration data from a run of the rotary machine deemed to be normal, and
  wherein the different amplitude thresholds are set by fitting an amplitude distribution to the training data points in each sub-range of vibration frequency and rotational speed;
  comparing each amplitude measurement to the amplitude threshold for a corresponding sub-range of vibration frequency and rotational speed for the data points within which the amplitude measurement falls;
  determining the amplitude measurement to represent noise if it falls below the amplitude threshold and as significant spectral content if it is above the amplitude threshold;
  using the amplitude measurement determined to be significant spectral content, assessing abnormalities of at least a component of the rotary machine; and
  when an abnormality is assessed, generating a signal configured to indicate the abnormality of at least a component of the rotary machine.

2. A method according to claim 1 wherein the different amplitude thresholds each representing a noise floor for a respective one of the first set of sub-ranges of vibration frequency and rotational speed are further set by
  calculating an extreme value distribution for said amplitude distribution and
  setting as said amplitude threshold an amplitude value representing a preset probability of being a maximum amplitude value that would be obtained for noise.

3. A method according to claim 2 wherein the preset probability is a probability above 0.99.

4. A method according to claim 2 wherein the amplitude distribution is a Gamma distribution.

5. A method according to claim 2 wherein the amplitude distribution is fitted after excluding training data points not representing background noise from the data in each sub-range of vibration frequency and rotational speed.

6. A method according to claim 2 further comprising:
  comparing each amplitude measurement to the extreme value distribution obtained from the training data points to read-off a probability value for that amplitude measurement;
  calculating from the probability value a novelty value as: novelty value=$-\log_{10}\{1-P_e(x)\}$, where $P_e(x)$ is the extreme value distribution as a function of amplitude x; and
  outputting the novelty value.

7. A method according to claim 1 further comprising:
  among a second set of sub-ranges of vibration frequency and rotational speed, determining which ones of the sub-ranges of the second set contained, during a training process using vibration data from a run of the rotary machine deemed to be normal, more than a preset number of training data points whose amplitude measurement was above the noise floor, and defining these ones of the sub-ranges of the second set of sub-ranges of vibration frequency and rotational speed as containing known significant spectral content; and
  for each amplitude measurement determined to represent significant spectral content, determining the amplitude measurement to represent known significant spectral content when the amplitude measurement is within a sub-range of the second set of sub-ranges of vibration frequency and rotational speed that contains known significant spectral content and to represent novel significant spectral content when the amplitude measurement is within a sub-range of the second set of sub-ranges that does not contain known significant spectral content.

8. A method according to claim 7 wherein the first set and the second set of sub-ranges of vibration frequency and rotational speed are the same.

9. A method according to claim 7 wherein an alarm condition is triggered if a threshold number of amplitude measurements representing novel significant spectral content are found or if amplitude measurements representing novel significant spectral content persist for a predetermined time.

10. A method according to claim 1 wherein the frequency range is divided into 30 to 120 sub-ranges and the rotational speed range is divided into 5 to 40 sub-ranges.

11. A method according to claim 1 wherein the frequency range is divided into 50 to 100 sub-ranges and the rotational speed range is divided into 10 to 30 sub-ranges.

12. Apparatus for monitoring vibration amplitude and frequency in a rotary machine, comprising inputs for receiving vibration measurements from a vibration sensor and measurements of the rotation speed of the machine from a tachometer, and a data processing system adapted to execute the method of claim 1.

13. A control system for a rotary machine comprising apparatus according to claim 12.

14. A method of monitoring vibration amplitude and frequency in a rotary machine, comprising the steps of:
receiving measurements of the vibration amplitude and the rotation speed of the machine from a run of the rotary machine from at least one sensor;
recording as a data point each amplitude measurement as a function of vibration frequency and rotational speed;
comparing each amplitude measurement to an amplitude threshold for a sub-range of vibration frequency and rotational speed for the data points within which the amplitude measurement falls,
wherein the amplitude threshold represents a noise floor for the sub-range of vibration frequency and rotational speed,
wherein the sub-range includes a sub-range of speeds and a sub-range of frequencies,
wherein the amplitude threshold is set in a training process using training data points comprising vibration data from a run of the rotary machine deemed to be normal, and
wherein the amplitude threshold is set by fitting an amplitude distribution to the training data points in the sub-range of vibration frequency and rotational speed;
determining a set of sub-ranges in which the amplitude measurement is above the amplitude threshold;
defining sub-ranges from the set of sub-ranges as known significant spectral content if more than a preset number of data points have an amplitude measurement above the amplitude threshold;
defining sub-ranges from the set of sub-ranges as novel significant spectral content if there is less than a preset number of data points having an amplitude measurement above the amplitude threshold;
using the sub-ranges defined to be novel significant spectral content, assessing abnormalities of at least a component of the rotary machine; and
when an abnormality is assessed, generating a signal configured to indicate the abnormality of at least a component of the rotary machine.

* * * * *